US 11,198,660 B2

(12) United States Patent
Dakka et al.

(10) Patent No.: US 11,198,660 B2
(45) Date of Patent: Dec. 14, 2021

(54) PRODUCTION OF METHYL-SUBSTITUTED BIPHENYL COMPOUNDS (71) Applicant: ExxonMobil Chemical Patents Inc., Baytown, TX (US)

(72) Inventors: Jihad M. Dakka, Whitehouse Station, NJ (US); Lorenzo C. Decaul, Langhorne, PA (US); Michael P. Lanci, Flemington, NJ (US); Wei Tang, New York, NY (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 412 days.

(21) Appl. No.: 16/073,494

(22) PCT Filed: Feb. 22, 2017

(86) PCT No.: PCT/US2017/018818
§ 371 (c)(1),
(2) Date: Jul. 27, 2018

(87) PCT Pub. No.: WO2017/180240
PCT Pub. Date: Oct. 19, 2017

(65) Prior Publication Data
US 2020/0325086 A1    Oct. 15, 2020

Related U.S. Application Data (60) Provisional application No. 62/321,802, filed on Apr. 13, 2016.

(30) Foreign Application Priority Data

Jun. 15, 2016 (EP) ..................... 16174549

(51) Int. Cl.
C07C 5/367 (2006.01)
C07C 5/10 (2006.01)
(Continued)

(52) U.S. Cl.
CPC ............. *C07C 5/367* (2013.01); *B01J 29/061* (2013.01); *B01J 29/7476* (2013.01); *C07C 5/10* (2013.01);
(Continued)

(58) Field of Classification Search
None
See application file for complete search history.

(56) References Cited

U.S. PATENT DOCUMENTS

| 4,123,470 A | 10/1978 | Murtha |
| 6,284,917 B1 | 9/2001 | Brunner et al. |

(Continued)

FOREIGN PATENT DOCUMENTS

| CN | 103664581 | 3/2014 | ............. C07C 51/36 |
| WO | 2003/029339 A | 4/2003 | |

(Continued)

OTHER PUBLICATIONS

Ninomiya, W., et al., "Dehydrogenation of Cycloalkanes Over Noble Metal Catalysts Supported on Active Carbon," Research on Chemical Intermediates, 2008, vol. 34, Nos. 8,9, pp. 663-668.

(Continued)

*Primary Examiner* — Philip Y Louie
*Assistant Examiner* — Alyssa L Cepluch (57) ABSTRACT In a process for producing a methyl-substituted biphenyl compound, at least one methyl-substituted cyclohexylbenzene compound of the formula:

$m(H_3C)$ —〔benzene ring〕—〔cyclohexyl ring〕— $(CH_3)_n$ (Continued)

wherein each of m and n is independently 1, 2, or 3, is contacted with hydrogen in the presence of a hydrogenation catalyst to produce a hydrogenation reaction product comprising at least one methyl-substituted bicyclohexane compound, and the methyl-substituted bicyclohexane compound is then contacted with a dehydrogenation catalyst to produce a dehydrogenation reaction product comprising at least one methyl-substituted biphenyl compound.

20 Claims, 5 Drawing Sheets

(51) Int. Cl.

| | |
|---|---|
| *C07C 15/14* | (2006.01) |
| *C07C 13/28* | (2006.01) |
| *C07C 5/13* | (2006.01) |
| *B01J 29/74* | (2006.01) |
| *B01J 29/06* | (2006.01) |

(52) U.S. Cl.
CPC ............... *C07C 5/13* (2013.01); *C07C 13/28* (2013.01); *C07C 15/14* (2013.01); *C07C 2523/14* (2013.01); *C07C 2529/70* (2013.01); *C07C 2529/74* (2013.01)

(56) References Cited

U.S. PATENT DOCUMENTS

| | | | |
|---|---|---|---|
| 6,730,625 | B1 | 5/2004 | Chang et al. |
| 6,740,254 | B2 | 5/2004 | Zhou et al. |
| 7,297,738 | B2 | 11/2007 | Goose et al. |
| 2006/0247461 | A1 | 11/2006 | Schlosberg et al. |
| 2008/0242895 | A1 | 10/2008 | Godwin et al. |
| 2010/0159177 | A1 | 6/2010 | Dakka et al. |
| 2012/0277472 | A1 | 11/2012 | Dakka et al. |
| 2014/0275605 | A1 | 9/2014 | Dakkat et al. |
| 2014/0275606 | A1 | 9/2014 | Bai et al. |
| 2014/0275607 | A1 | 9/2014 | Dakka et al. |
| 2014/0275609 | A1 | 9/2014 | Dakka et al. |
| 2015/0080545 | A1 | 3/2015 | Dakka et al. |

FOREIGN PATENT DOCUMENTS

| | | | |
|---|---|---|---|
| WO | 2004/046078 A | 6/2004 | |
| WO | WO2010-038633 | 4/2010 | ............ C07C 51/36 |
| WO | 2015/134059 A | 9/2015 | |

OTHER PUBLICATIONS

Castano, P., et al., "Kinetic and Deactivation Modelling of Biphenyl Liquid-phase Hydrogenation over Bimetallic Pt—Pd Catalyst," Applied Catalysis B: Environmental, 2009, vol. 88, No. 1, pp. 213-223.

Kulev, L.P., et al., "Esters of diphenic acid and their plasticizing properties," Izvestiya Tomskogo Politekhnicheskogo Instituta, 1961, p. 111.

Shioda H., et al., "Studies on the Syntheses of Dialkyl Diphenates and Their Properties," Yuki, 1959 Gosei Kagaku Kyokaishi. pp. 91-93, Journal of Synthetic Organic Chemistry, Japan.

Godwin, "Plasticizers," Applied Polymer Science 21st Century, Edited by Craver et al., Elsevier, 2000, pp. 157-175.

Chen, J.C., et al., "Direct Alkylation of Aromatic Hydrocarbons with n-Paraffin", DAN 97M-1094, Dec. 1, 1997.

Stevenson, S., et al. "Conversion of Benzene to Phenylcyclohexane over a Tungsten/Zirconia Catalyst", DAN 97M-0392, May 7, 1997.

PRODUCTION OF METHYL-SUBSTITUTED BIPHENYL COMPOUNDS

CROSS-REFERENCE OF RELATED APPLICATIONS

This application is a National Phase Application claiming priority to PCT Application Serial No. PCT/US2017/018818 filed Feb. 22, 2017, which claims priority to and the benefit of U.S. Ser. No. 62/321,802, filed Apr. 13, 2016, and EP application 16174549.2, filed Jun. 15, 2016, the disclosures of which are incorporated herein by reference.

FIELD OF THE INVENTION

The disclosure relates to methyl-substituted biphenyl compounds, their production and, their use in the manufacture of plasticizers.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

There is a need for mono- or diester plasticizers, particularly oxo-ester plasticizers, that can be made from low cost feeds and employ few manufacturing steps in order to have good economics. An example of previous plasticizers made from low cost feed are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, U.S. 2006/0247461, and U.S. Pat. No. 7,297,738.

Other suggested plasticizers include esters based on benzoic acid (see, for instance, U.S. Pat. No. 6,740,254) and polyketones, such as described in U.S. Pat. No. 6,777,514; and U.S. 2008/0242895. Epoxidized soybean oil, which has much longer alkyl groups ($C_{16}$ to $C_{18}$), has been tried as a plasticizer, but is generally used as a PVC stabilizer. Stabilizers are used in much lower concentrations than plasticizers. US Patent Publication No. 2010-0159177 discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

Other suggested plasticizers further include biphenic esters. For example, in an article entitled "Esters of diphenic acid and their plasticizing properties," Kulev et al., *Izvestiya Tomskogo Politekhnicheskogo Instituta* (1961) 111, disclose that diisoamyl diphenate, bis(2-ethylhexyl) diphenate and mixed heptyl, octyl and nonyl diphenates can be prepared by esterification of diphenic acid, and allege that the resultant esters are useful as plasticizers for vinyl chloride. Similarly, in an article entitled "Synthesis of dialkyl diphenates and their properties," Shioda et al., *Yuki Gosei Kagaku Kyokaishi* (1959), 17, disclose that dialkyl diphenates of $C_1$ to $C_8$ alcohols, said to be useful as plasticizers for poly(vinyl chloride), can be formed by converting diphenic acid to diphenic anhydride and esterifying the diphenic anhydride. However, since these processes involve esterification of diphenic acid or anhydride, they necessarily result in 2,2'-substituted diesters of diphenic acid. Generally, such diesters having substitution on the 2-carbons have proven to be too volatile for use as plasticizers.

An alternative method of producing dialkyl diphenate esters having an increased proportion of the desired less volatile 3,3', 3,4' and 4,4' diesters has recently been developed. In particular, it has been found that dimethyl biphenyl compounds containing significant amounts of the 3,3'-dimethyl, the 3,4'-dimethyl and the 4,4'-dimethyl isomers can be economically produced by hydroalkylation of toluene and/or xylene followed by catalyst dehydrogenation of the resulting (methylcyclohexyl)toluene and/or (dimethylcyclohexyl)xylene product. U.S. 2014/0275605, U.S. 2014/0275606, U.S. 2014/0275607, and U.S. 2014/0275609 describe these hydroalkylation and dehydrogenation steps. The resultant mixture can then be used as a precursor in the production of biphenylester-based plasticizers by, for example, oxidizing the methyl-substituted biphenyl compounds to convert at least one of the methyl groups to a carboxylic acid group and then esterifying the carboxylic acid group(s) with an alcohol, such as an oxo alcohol.

However, it has been observed in the dehydrogenation step that the initial conversion of the hydroalkylation product, e.g., (methylcyclohexyl)toluene (MCHT) to the desired dimethyl biphenyl (DMBP) products can be low, e.g., about 85% or less, and that catalyst deactivation is also a challenge. Without wishing to be bound by theory, it is believed that the observed low conversion is caused in part by the low reactivity and conversion of 2, X' isomers due to steric hindrance and the low surface absorption of these isomers and also caused in part by the lack aromatic ring formation in the dehydrogenation of 1, X' isomers. The combination of these effects is thought to result in yield loss and complicates the separation of the desired products. Thus, there is a need for a process of producing methyl-substituted biphenyl compounds with improved conversion to the desired products and reduced deactivation of the dehydrogenation catalyst.

SUMMARY OF THE INVENTION

Accordingly, in one aspect, the present disclosure relates to a process for producing methyl-substituted biphenyl compounds having improved yield of desired products and reduced deactivation of the dehydrogenation catalyst. The methyl-substituted biphenyl compounds are formed from at least one methyl-substituted cyclohexylbenzene compound of the formula (I):

(I)

wherein each of m and n is independently 1, 2, or 3. The process comprises hydrogenating the methyl-substituted cyclohexylbenzene compound(s) to produce a hydrogenation reaction product comprising at least one methyl-substituted bicyclohexane compound, followed by dehydrogenating the methyl-substituted bicyclohexane compound(s) to form a dehydrogenation reaction product comprising the desired methyl-substituted biphenyl compounds.

The hydrogenation reaction product comprises less than about 30 wt % of 1, X'- and/or 2-X'-isomers (where X' is 2', 3', or 4') of methyl-substituted bicyclohexane based on the total weight of the isomers of methyl-substituted bicyclohexane. Preferably, the hydrogenation reaction product comprises less than about 20 wt % of 2, X' isomers of methyl-substituted bicyclohexane based on the total weight of the isomers of methyl-substituted bicyclohexane. The dehydrogenation reaction product comprises less than about 20 wt % of 2, X' isomers (where X' is 2', 3', or 4') based on the total weight of the isomers of the methyl-substituted biphenyl compounds.

Often, the present process may further comprise contacting at least part of the dehydrogenation reaction product with an oxygen source under conditions effective to convert at least part of the methyl-substituted biphenyl compounds to biphenyl carboxylic acids and reacting the biphenyl carboxylic acids with one or more $C_4$ to $C_{14}$ alcohols under conditions effective to produce biphenyl esters. In another aspect, the present invention relates to a composition comprising less than about 30 wt %, such as less than about 20 wt %, of 2-X'-isomers (where X' is 2', 3', or 4') of dimethylbicyclohexane and/or tetramethylbicyclohexane based on the total weight of isomers of dimethylbicyclohexane and/or tetramethylbicyclohexane of the composition.

DETAILED DESCRIPTION OF THE INVENTION

Described herein is a process for producing methyl-substituted biphenyl compounds useful as precursors in the manufacture of biphenyl ester plasticizers. As discussed below, the process involves the catalytic hydrogenation of methyl-substituted cyclohexylbenzene compounds to methyl-substituted bicyclohexane compounds followed by the catalytic dehydrogenation of at least part of the hydrogenation reaction product. The methyl-substituted cyclohexylbenzene compounds can be provided by catalytic hydroalkylation of alkylbenzenes, such as toluene and/or xylene. The present inventors have surprisingly found that utilizing a hydrogenation step to convert the methyl-substituted cyclohexylbenzene compounds to methyl-substituted bicyclohexane compounds prior to dehydrogenation of the resulting methyl-substituted bicyclohexane compounds unexpectedly improves the yield of desired methyl-substituted biphenyl compounds and slows the deactivation of the dehydrogenation catalyst. Not wishing to be bound by theory, it is believed that isomerization of the methyl-substituted cyclohexylbenzene occurs simultaneously during the hydrogenation, resulting in isomers of methyl-substituted bicyclohexane compounds that can be readily dehydrogenated. In particular, it has been found that isomerization of 1, X'- and/or 2, X'-isomers may occur during the hydrogenation of the hydroalkylation product, resulting in reduced amounts of isomers having a methyl group in the 1 or 2 positions in the hydrogenation product.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a $C_{12}$+ component" should be interpreted to include one, two or more $C_{12}$+ components unless specified or indicated by the context to mean only one specific $C_{12}$+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, the term "$C_n$," hydrocarbon wherein n is a positive integer, e.g., 1, 2, 3, 4, etc., means a hydrocarbon having n number of carbon atom(s) per molecule. The term "$C_n$+" hydrocarbon wherein n is a positive integer, e.g., 1, 2, 3, 4, etc., as used herein, means a hydrocarbon having at least n number of carbon atom(s) per molecule. The term "$C_n-$" hydrocarbon wherein n is a positive integer, e.g., 1, 2, 3, 4, etc., used herein, means a hydrocarbon having no more than n number of carbon atom(s) per molecule.

Hydroalkylation of Toluene and/or Xylene

Hydroalkylation is a two-stage catalytic reaction in which an aromatic compound is partially hydrogenated to produce a cyclic olefin, which then reacts, in situ, with the aromatic compound to produce a cycloalkylaromatic product. In the present process, the aromatic feed comprises toluene and/or xylene and the cycloalkylaromatic product comprises a mixture of (methylcyclohexyl)toluene and/or (dimethylcyclohexyl)xylene isomers. In the case of toluene, the desired reaction may be summarized as follows:

The isomers of (methylcyclohexyl)toluene formed during the hydroalkylation of toluene are illustrated as below, in which X' is 3', 4', and 2', respectively, from top to bottom in each column.

| 4, X'-isomers |
| --- |

1-methyl-4-(4-methylcyclohexyl)benzene 1-methyl-3-(4-methylcyclohexyl)benzene 1-methyl-2-(4-methylcyclohexyl)benzene

| 3, X'-isomers |
| --- |

1-methyl-4-(3-methylcyclohexyl)benzene 1-methyl-3-(3-methylcyclohexyl)benzene 1-methyl-2-(3-methylcyclohexyl)benzene

| 2, X'-isomers |
| --- |

1-methyl-4-(2-methylcyclohexyl)benzene

1-methyl-3-(2-methylcyclohexyl)benzene 1-methyl-2-(2-methylcyclohexyl)benzene

| 1, X'-isomers |
| --- |

1-methyl-4-(1-methylcyclohexyl)benzene 1-methyl-3-(1-methylcyclohexyl)benzene

-continued 1-methyl-2-(1-methylcyclohexyl)benzene

When the methyl group is located in the 1 position (quaternary carbon) on the cyclohexyl ring, ring isomerization can occur forming (dimethylcyclopentyl)toluene and (ethylcyclopentyl)toluene which, upon dehydrogenation, will generate diene by-products that are difficult to separate from the desired product and will also inhibit the subsequent oxidation reaction. In the oxidation and esterification steps, different isomers have different reactivity. Specifically, para-isomers are more reactive than meta-isomers which are more reactive than ortho-isomers. In addition, the presence of a methyl group in the 2 position on either the cyclohexyl or phenyl ring is a precursor for the formation of fluorene and methyl fluorene during dehydrogenation. Fluorene is difficult to separate from the dimethylbiphenyl product and causes problems in the oxidation step and also in plasticizer performance. It is therefore advantageous to minimize the formation of isomers which have a methyl group in the ortho, 2 and benzylic positions.

A competing reaction to the desired hydroalkylation is dialkylation in which the (methylcyclohexyl)toluene product reacts with further methylcyclohexane to produce di(methylcyclohexyl)toluene according to the following reactions:

This dialkylated by-product can be converted back to (methylcyclohexyl)toluene, in this case by transalkylation. However, this process requires the use of an acid catalyst at temperatures above 160° C. and can lead to the production of additional by-products, such as di(methylcyclopentyl) toluenes, cyclohexylxylenes and cyclohexylbenzene. It is therefore desirable to employ a hydroalkylation catalyst that exhibits low selectivity towards di(methylcyclohexyl)toluene and other heavy by-products.

The catalyst employed in the hydroalkylation reaction is a bifunctional catalyst comprising a hydrogenation component and a solid acid alkylation component, typically a molecular sieve. The catalyst may also include a binder such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the hydroalkylation catalyst. Suitable metals include palladium (Pd), ruthenium (Ru), nickel (Ni), zinc (Zn), tin (Sn), and cobalt (Co), with palladium being particularly advantageous. Often, the amount of hydrogenation metal present in the catalyst is between about 0.05 wt % and about 10 wt %, such as between about 0.1 wt % and about 5 wt %, of the catalyst.

Often, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and U.S. Re. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Alternatively and preferably, the solid acid alkylation component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and/or xylene and hydrogen, a diluent, which is substantially inert under hydroalkylation conditions, may be supplied to the hydroalkylation reaction. Often, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The aromatic feed to the hydroalkylation reaction may also include benzene and/or one or more alkylbenzenes different from toluene and xylene. Suitable alkylbenzenes may have one or more alkyl groups with up to 4 carbon atoms and include, by way of example, ethylbenzene, cumene, and unseparated $C_6$-$C_8$ or $C_7$-$C_8$ or $C_7$-$C_9$ streams.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa. The molar ratio of hydrogen to aromatic feed is typically from about 0.15:1 to about 15:1.

In the present process, it has been found that molecular sieves of the MCM-22 family are particularly active and stable catalysts for the hydroalkylation of toluene or xylene. In addition, catalysts containing molecular sieves of the MCM-22 family exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it has been found that the hydroalkylation reaction product may comprise:

at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers;

less than 30 wt % of methylcyclohexane and less than 2% of dimethylbicyclohexane compounds;

and less than 1 wt % of dialkylated $C_{21}$+ compounds.

Similarly, with a xylene feed, the hydroalkylation reaction product may comprise less than 1 wt % of compounds containing in excess of 16 carbon atoms.

Hydrogenation of Hydroalkylation Product

The major components of the hydroalkylation reaction effluent are (methylcyclohexyl)toluenes and/or (dimethylcyclohexyl)xylenes, unreacted aromatic feed (toluene and/or xylene), fully saturated single ring by-products (methylcyclohexane and dimethylcyclohexane), and some dialkylated $C_{21}$+ compounds. The unreacted feed and light by-products can readily be removed from the reaction effluent by, for example, distillation. The unreacted feed can then be recycled to the hydroalkylation reactor, while the saturated by-products can be dehydrogenated to produce additional recyclable feed. In the present process, some or all of the dialkylated $C_{21}$+ compounds are also removed from the hydroalkylation reaction effluent, in the same or a separate distillation step, so that the feed to the subsequent treating step comprises less than 0.5 wt %, such as less than 0.25 wt %, such as less than 0.1 wt %, even no detectable amount, of the dialkylated $C_{21}$+ compounds.

The remainder of the hydroalkylation reaction effluent, mainly composed of (methylcyclohexyl)toluene and/or (dimethylcyclohexyl)xylene isomers, can be hydrogenated to produce dimethylbicyclohexanes and/or tetramethylbicyclohexanes. The hydrogenation is to conveniently conducted at a temperature from about 50° C. to about 400° C., such as from about 100° C. to about 300° C. and a pressure from about 100 kPa to about 10000 kPa (atmospheric to about 1500 psig), such as from about 1000 kPa to about 8000 kPa, in the presence of a hydrogenation catalyst.

A suitable hydrogenation catalyst can comprise a hydrogenation metal or compound thereof supported on an inorganic substrate. Any known hydrogenation metal may be employed in the hydroalkylation catalyst, specific, non-limiting suitable examples of which include Pd, Pt, Rh, Ru, Os, Ir, Ni, Zn, Sn, Co, with Pd and/or Pt being particularly advantageous. Desirably, the amount of hydrogenation metal present in the hydrogenation catalyst is from about 0.05 wt % to about 10.0 wt %, such as from about 0.10 wt % to about 5.0 wt %, of the total weight of the hydrogenation catalyst. Specific, non-limiting examples of suitable inorganic substrates include $Al_2O_3$ and/or $SiO_2$ and refractory supports described herein. Conveniently, the hydroalkylation catalyst can be used as the hydrogenation catalyst so long as the hydrogenation conditions are changed to effectively conduct hydrogenation.

The product of the hydrogenation step comprises: at least about 70 wt %, preferably at least about 80 wt %, and ideally at least about 90 wt % of the 3,3'-, 3,4'-, 4,3'- and 4,4'-isomers; less than about 10 wt %, preferably less than about 8 wt %, and ideally less than about 7 wt % of 1, X' isomers; and less than about 20 wt %, preferably less than about 15 wt %, and ideally less than about 13 wt % 2, 3' and 2, 4'-isomers of methyl-substituted bicyclohexane compounds based on the total weight of all the methyl-substituted bicyclohexane isomers according to $^{13}$C NMR analysis. Often, the total amount of 1,X'- and 2,X'-isomers of methyl-substituted bicyclohexanes is less than about 30 wt %, preferably less than about 25 wt %, and ideally less than about 20% of the total isomers. In addition, the hydrogenation product may contain less than about 10 wt %, preferably less than about 5 wt %, and ideally less than about 3 wt % of methyl-substituted biphenyl compounds and less than about 5 wt %, preferably less than about 3 wt %, and ideally less than about 1 wt % of fluorene and methyl fluorenes combined.

Dehydrogenation of Hydrogenation Product

The hydrogenation product mainly comprises saturated methyl-substituted bicyclohexane isomers, and can be fed directly to the dehydrogenation step to produce the corresponding methyl-substituted biphenyl compounds. Optionally, non-bicyclohexane isomers present in the hydrogenation product can be separated prior to dehydrogenation. The dehydrogenation is conveniently conducted at a temperature from about 200° C. to about 600° C. and a pressure from about 100 kPa to about 3550 kPa (atmospheric to about 500 psig) in the presence of a dehydrogenation catalyst.

A suitable dehydrogenation catalyst can comprise one or more elements or compounds thereof selected from Group 10 of the Periodic Table of Elements, for example platinum, optionally supported on a refractory support. Often, the Group 10 element is present in an amount from about 0.1 wt % to about 5 wt % of the catalyst. In some cases, the dehydrogenation catalyst may also include tin or a tin compound to improve the selectivity to the desired methyl-substituted biphenyl product. Preferably, the tin is present in amount from about 0.05 wt % to about 2.5 wt % of the dehydrogenation catalyst.

Suitable dehydrogenation catalyst supports are refractory in the sense that they are capable of withstanding the conditions employed in the dehydrogenation reaction without physical or chemical changes. Non-limiting examples of suitable refractory support materials include: alumina; silica; silica-alumina; titania; calcium oxide; strontium oxide; barium oxide; magnesium oxide; carbon; zirconia; diatomaceous earth; lanthanide oxides including cerium oxide; lanthanum oxide; neodynium oxide; yttrium oxide and praesodynium oxide; oxides of chromium, thorium, uranium, niobium and tantalum; tin oxide; zinc oxide; and aluminum phosphate. Suitable refractory acidic supports for the dehydrogenation catalyst comprise one or more of alumina, silica-alumina, zirconia, titania, and lanthanide oxides, with alumina being preferred. Other useful supports can be those as described in U.S. Patent Application Publication No. 2014/0275607, the content of which is incorporated herein by reference.

Where the dehydrogenation catalyst contains tin, the catalyst may be prepared by impregnating the support with an aqueous solution of a suitable tin compound, such as tin chloride and/or tin tartrate. The impregnated support containing tin is then dried in air, such as at 120° C. for 4 hrs, and then calcined, such as at 538° C. in air for 3 hrs, to convert the tin to an oxide form. Afterwards, platinum is added to the tin-containing support by impregnation with an aqueous solution of a suitable platinum compound, such as $(NH_3)_4Pt(NO_3)_2$. The sample containing tin and platinum is then dried in air, such as at 120° C. for 4 hrs, and then calcined, such as at 360° C. in air for 3 hrs.

The dehydrogenation product comprises methyl-substituted biphenyl compounds in which the concentration of the 3,3'-, 3,4'- and 4,4'-isomers is at least about 70 wt %, preferably at least about 80 wt %, and ideally at least about 90 wt % based on the total weight of the methyl-substituted biphenyl isomers. The conversion rate of bicyclohexanes in the hydrogenation product to methyl-substituted biphenyl compounds may be greater than about 90%, preferably greater than about 95%, and ideally greater than about 98%.

The dehydrogenation product may further comprise unreacted methyl-substituted cyclohexylbenzene and/or 2, X'-isomers (where X' is 2', 3', or 4') of methyl-substituted biphenyl compounds. The 2, X'-isomers of methyl-substituted biphenyl compounds are generally present in an amount of less than about 20 wt %, preferably less than 15 wt %, and ideally less than about 10 wt % based on the total weight of the methyl-substituted biphenyl isomers. The unreacted methyl-substituted cyclohexylbenzene can be separated from the dehydrogenation product by means of any known methods, such as distillation, and then recycled to the dehydrogenation reaction or to the hydrogenation reaction as described herein above. The 2, X'-isomers of methyl-substituted biphenyl compounds can be also separated from the dehydrogenation product by, for example, the same or different distillation and then recycled to the hydrogenation reaction as described herein above.

Production of Biphenyl Esters

The methyl-substituted biphenyl compounds produced by the dehydrogenation reaction can readily be converted ester plasticizers by a process comprising oxidation to produce the corresponding carboxylic acids followed by esterification with an alcohol. The oxidation can be performed by any process known in the art, such as by reacting the methyl-substituted biphenyl compounds with an oxidant, such as oxygen, ozone or air, or any other oxygen source, such as hydrogen peroxide, in the presence of a catalyst at temperatures from 30° C. to 300° C., such as from 60° C. to 200° C. Suitable catalysts comprise Co or Mn or a combination of both metals.

The resulting carboxylic acids can then be esterified to produce biphenyl ester plasticizers by reaction with one or more $C_4$ to $C_{14}$ alcohols. Suitable esterification conditions are well-known in the art and include, but are not limited to, temperatures of 0-300° C. and the presence or absence of homogeneous or heterogeneous esterification catalysts, such as Lewis or Bronsted acid catalysts. Suitable alcohols are "oxo-alcohols," by which is meant an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. Another source of olefins used in the OXO process are through the oligomerization of ethylene, producing mixtures of predominately straight chain alcohols with lesser amounts of lightly branched alcohols. The biphenyl ester plasticizers of the present application find use in a number of different polymers, such as vinyl chloride resins, polyesters, polyurethanes, ethylene-vinyl acetate copolymers, rubbers, poly (meth)acrylics and mixtures thereof.

Process

Figure 1:
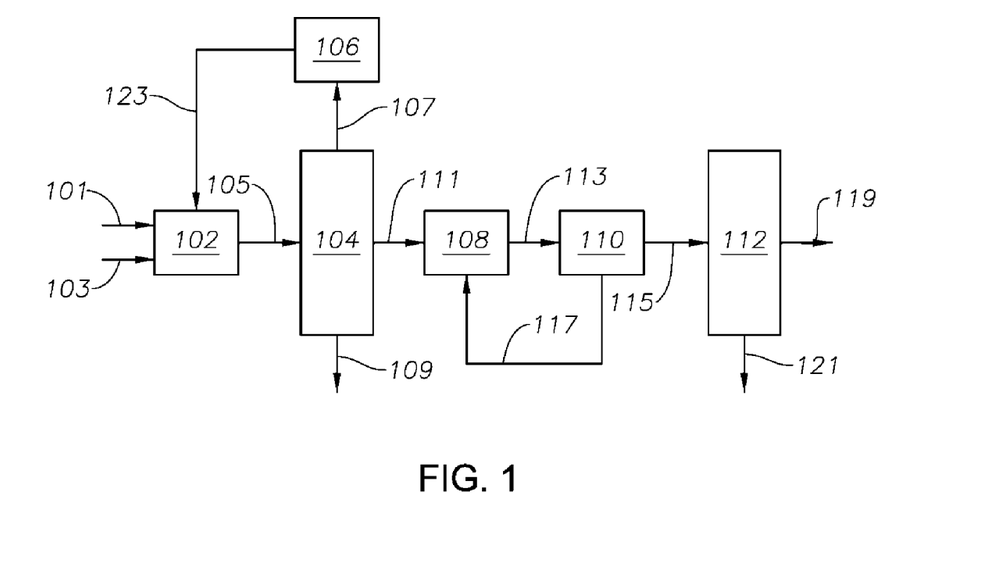
FIG. 1 is a diagram of a process of making methyl-substituted biphenyl compounds.
Figure 2:
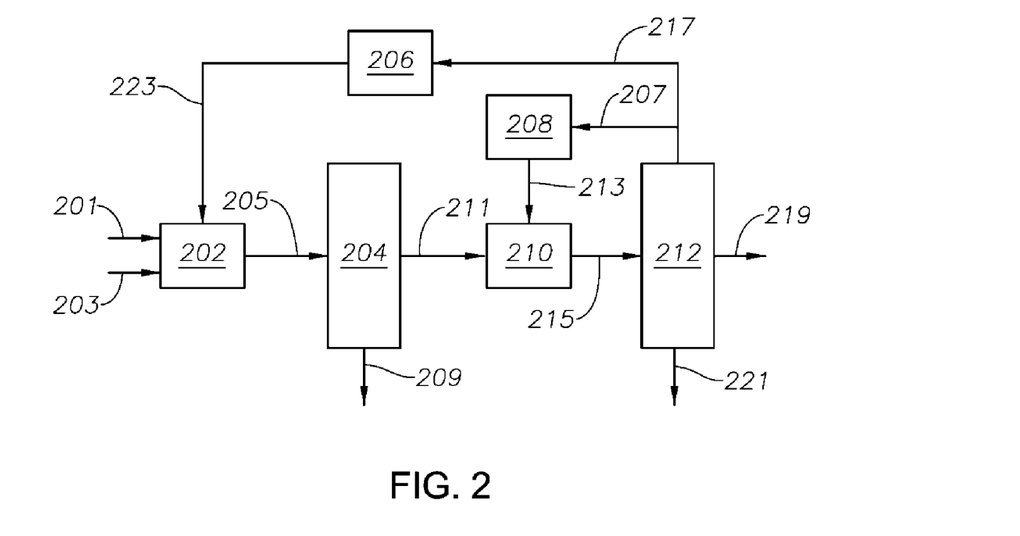
FIG. 2 is a diagram of an alternative process of making methyl-substituted biphenyl compounds.

The present inventive process will now be more particularly described with reference to FIGS. 1 and 2. FIG. 1 illustrates one aspect of the present inventive process, in which the hydroalkylation product is subjected to hydrogenation followed by dehydrogenation. FIG. 2 illustrates an alternative aspect of the present inventive process, in which the hydroalkylation product is first dehydrogenated, after which unreacted methyl-substituted cyclohexylbenzene, and advantageously the 2,X'-isomers, are separated and hydrogenated. A resulting hydrogenated effluent is recycled to the dehydrogenation step. A further detailed description will now be made with reference to toluene as the aromatic hydrocarbon feed.

As shown in FIG. 1, a toluene stream 101 and a hydrogen stream 103 are fed to a hydroalkylation reactor 102 to produce a hydroalkylation effluent 105 comprising (methylcyclohexyl)toluene, unreacted toluene, and byproducts, e.g., methylcyclohexane and dialkylates. The hydroalkylation effluent is then fed to a separator 104, e.g., a distillation column, to separate a light fraction 107 comprising unreacted toluene and methylcyclohexane, and a heavy fraction 109 comprising dialkylates from the hydroalkylation effluent. The resulting obtained fraction 111 is mainly composed of (methylcyclohexyl)toluene isomers. The light fraction 107 can be fed to a dehydrogenation reactor 106 to convert the methylcyclohexane to toluene, after which the dehydrogenation effluent 123 from reactor 106 can be recycled to the hydroalkylation reactor 102. Preferably, the heavy fraction 109 may be subjected to transalkylation to convert the dialkylates to (methylcyclohexyl)toluene (not shown). Fraction 111 is then introduced to a hydrogenation reactor 108 to produce a hydrogenation effluent 113, which is mainly composed of dimethylbicyclohexanes. The hydrogenation effluent 113 can then be fed to a dehydrogenation reactor 110 to produce a dehydrogenation effluent 115, which mainly comprises dimethylbiphenyls and heavy byproducts, such as methylfluorene. A hydrogen stream 117 generated in the dehydrogenation reactor 110 can be recycled to the hydrogenation reactor 108. The dehydrogenation effluent 115 is then fed to a separator 112 to obtain a dimethylbiphenyl fraction 119 and a heavy fraction 121. The dimethylbiphenyl fraction 119 is then sent to downstream treatment for production of biphenyl esters (not shown).

As shown in FIG. 2, a toluene stream 201 and hydrogen stream 203 are fed to a hydroalkylation reactor 202 to produce a hydroalkylation effluent 205 comprising (methylcyclohexyl)toluene, unreacted toluene, and byproducts, e.g., methylcyclohexane and dialkylates. The hydroalkylation effluent is then fed to a separator 204, e.g., a distillation column, to separate a heavy fraction 209 comprising dialkylates from the hydroalkylation product. The resulting obtained fraction 211 is mainly composed of (methylcyclohexyl)toluene isomers, light by-product, such as methylcyclohexane, and unreacted toluene. The heavy fraction 209 may be subjected to transalkylation to convert the dialkylates to (methylcyclohexyl)toluene (not shown). Fraction 211 is then introduced to a dehydrogenation reactor 210 to produce a dehydrogenation effluent 215, which mainly comprises dimethylbiphenyls, unreacted methylcyclotoluene (such as 1, X'-isomers), unreacted toluene, heavy by-products (such as methylfluorene), etc. The dehydrogenation effluent 215 is then fed to a separator 212 to obtain a first light fraction 217, a second light fraction 207, a dimethylbiphenyl fraction 219, and a heavy fraction 221. The first light fraction 217, comprising unreacted toluene and methylcyclohexane, can be fed to a dehydrogenation reactor 206 to convert the methylcyclohexane to toluene, after which the dehydrogenation effluent 223 from reactor 206 can be recycled to the hydroalkylation reactor 202. The second light fraction 207, mainly comprising unreacted (methylcyclohexyl)toluene and, advantageously 2, X'-isomers of dimethylbiphenyl compounds, can be hydrogenated in reactor 208 to convert at least part of the (methylcyclohexyl)toluene and 2, X'-isomers to form a dimethylbicyclohexane stream 213, which can be fed to dehydrogenation reactor 210 for further dehydrogenation. The dimethylbiphenyl fraction 219, mainly comprising 3, X'- and 4, X'-isomers, is then sent to downstream treatment for production of biphenyl esters (not shown). The invention will now be more particularly described with reference to the accompanying drawings and the following non-limiting Examples.

Example 1: Synthesis of 0.3% Pd/MCM-49 Hydroalkylation Catalyst 80 parts MCM-49 zeolite crystals are combined with 20 parts pseudoboehmite alumina, on a calcined dry weight basis. The MCM-49 and pseudoboehmite alumina dry powder is placed in a muller and mixed for about 10 to 30 minutes. Sufficient water and 0.05% polyvinyl alcohol is added to the MCM-49 and alumina during the mixing process to produce an extrudable paste. The extrudable paste is formed into a $1/20$ inch (0.13 cm) quadrulobe extrudate using an extruder and the resulting extrudate is dried at a temperature ranging from 250° F. to 325° F. (120° C. to 163° C.). After drying, the dried extrudate is heated to 1000° F. (538° C.) under flowing nitrogen. The extrudate is then cooled to ambient temperature and humidified with saturated air or steam.

After the humidification, the extrudate is ion exchanged with 0.5 to 1 N ammonium nitrate solution. The ammonium nitrate solution ion exchange is repeated. The ammonium nitrate exchanged extrudate is then washed with deionized water to remove residual nitrate prior to calcination in air. After washing the wet extrudate, it is dried. The exchanged and dried extrudate is then calcined in a nitrogen/air mixture to a temperature 1000° F. (538° C.). Afterwards, the calcined extrudate is cooled to room temperature. The 80% MCM-49, 20% $Al_2O_3$ extrudate was incipient wetness impregnated with a palladium (II) chloride solution (target: 0.30% Pd) and then dried overnight at 121° C. The dried catalyst was calcined in air at the following conditions: 5 volumes air per volume catalyst per minute, ramp from ambient to 538° C. at 1° C./min and hold for 3 hours.

Example 2: Preparation of 1% Pt/0.15% $Sn/SiO_2$ Dehydrogenation Catalyst

A 1% Pt/0.15% $Sn/SiO_2$ catalyst was prepared by incipient wetness impregnation, in which a 1/20" (1.2 mm) quadrulobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. The resultant product was calcined in air at 350° C. for 3 hours before being used in subsequent catalyst testing.

Example 3: Hydroalkylation of Toluene

A toluene feed was hydroalkylated using the catalyst of Example 1 using the reactor and process described below.

The reactor comprised a stainless steel tube having an outside diameter of: 3/8 inch (0.95 cm), a length of 20.5 inch (52 cm) and a wall thickness of 0.35 inch (0.9 cm). A piece of stainless steel tubing having a length of 8 3/4 inch (22 cm) and an outside diameter of 3/8 inch (0.95 cm) enveloping a similar length tubing having an outside diameter of 1/4 inch (0.6 cm) was used in the bottom of the reactor as a spacer to position and support the catalyst in the isothermal zone of the furnace. A ¼ inch (0.6 cm) plug of glass wool was placed on top of the spacer to keep the catalyst in place. A ⅛ inch (0.3 cm) stainless steel thermo-well was placed in the catalyst bed to monitor temperature throughout the catalyst bed using a movable thermocouple.

The catalyst was sized to 20/40 sieve mesh or cut to a 1:1 length to diameter ratio, dispersed with quartz chips (20/40 mesh) then loaded into the reactor from the top to a volume of 5.5 cc. The catalyst bed was typically 12.5 cm. in height. The catalyst was then loaded into the reactor from the top. The catalyst bed was 15 cm. in length. A ¼ plug of glass wool was placed on top of the catalyst bed and used to separate quartz chips from the catalyst. The remaining void space at the top of the reactor was filled with quartz chips. The reactor was installed in a furnace with the catalyst bed in the middle of the furnace at a pre-marked isothermal zone. The reactor was then pressure and leak tested, typically at 300 psig (2170 kPa).

The catalyst was pre-conditioned in situ by heating to 25° C. to 240° C. with $H_2$ flow at 100 cc/min and holding for 12 hours. A 500 cc ISCO syringe pump was used to introduce a chemical grade toluene feed to the reactor. The feed was pumped through a vaporizer before flowing through heated lines to the reactor. A Brooks mass flow controller was used to set the hydrogen flow rate. A Grove "Mity Mite™" back pressure controller was used to control the reactor pressure, typically at 150 psig (1135 kPa). GC analyses were taken to verify feed composition. The feed was then pumped through the catalyst bed held at the reaction temperature of 120° C. to 180° C. at a weight hourly space velocity (WHSV) of 2 and a pressure of 15-200 psig (204-1480 kPa). The liquid products exiting the reactor flowed through heated lines routed to two collection pots in series, the first pot being heated to 60° C. and the second pot cooled with chilled coolant to about 10° C. Material balances were taken at 12 to 24 hr intervals. Samples were taken and diluted with 50% ethanol for analysis. A Hewlett Packard 6890 gas chromatograph with FID detector was used for the analysis. The non-condensable gas products were routed to an on line HP 5890 GC.

The following procedure was used for GC analyses of the hydroalkylation product, using a chemical grade toluene. Two grams of catalyst, sized to a length of about 1/16 inch (0.15 cm) were diluted with sand to 5.5 cc of a catalyst/sand mixture. (6.5 cc. when self-bound 1/16" quadrulobe was used). The mixture was charged to a down-flow, fixed-bed reactor having an outer diameter of ⅜" inch (0.95 cm). The catalyst was pretreated with 50 cc/min of flowing hydrogen for 2 hours at 300° C. and 1 atm. After cooling to 120° C. in flowing hydrogen at 21 cc/min, toluene was fed to the reactor through an ISCO pump, the reactor pressure was increased to 150 psig (1136 kPa). The toluene flow rate was reduced to 2 WHSV (2:1 hydrogen/benzene molar ratio). Liquid products were collected in a cold product trap for analysis.

Example 4: Dehydrogenation of (Methylcyclohexyl)Toluene (Comparative)

A (methylcyclohexyl)toluene feed was dehydrogenated using the catalyst of Example 2 using the reactor and process described below.

The reactor comprised a stainless steel tube having an outside diameter of ⅜ inch (0.95 cm), a length of 20.5 inch (52 cm) and a wall thickness of 0.35 inch (0.9 cm). A piece of stainless steel tubing having a length of 8¾ inch (22 cm) and an outside diameter of ⅜ inch (0.95 cm) enveloping a similar length tubing having an outside diameter of ¼ inch (0.6 cm) was used in the bottom of the reactor as a spacer to position and support the catalyst in the isothermal zone of the furnace. A ¼ inch (0.6 cm) plug of glass wool was placed on top of the spacer to keep the catalyst in place. A ⅛ inch (0.3 cm) stainless steel thermo-well was placed in the catalyst bed to monitor temperature throughout the catalyst bed using a movable thermocouple. The catalyst was loaded with a spacer at the bottom to keep the catalyst bed in the center of the furnace's isothermal zone.

The catalyst of Example 2 was sized to 20/40 sieve mesh or cut to a 1:1 length to diameter ratio, dispersed with quartz chips (20/40 mesh) then loaded into the reactor from the top to a volume of 5.5 cc. When loaded, the catalyst bed measured about 12.5 cm in height. The reactor was topped off with the same size quartz or a larger size up to 14 mesh. The reactor was installed in the furnace with the catalyst bed in the middle of the furnace at the pre-marked isothermal zone. The reactor was then pressure and leak tested, typically at 300 psig (2170 kPa).

The catalyst was pre-conditioned in situ by heating to 375° C. to 460° C. with $H_2$ flow at 100 cc/min and holding for 2 hours. A 500 cc ISCO syringe pump was used to introduce a chemical grade toluene feed to the reactor. The feed was pumped through a vaporizer before flowing through heated lines to the reactor. A Brooks mass flow controller was used to set the hydrogen flow rate. A Grove "Mity Mite™" back pressure controller was used to control the reactor pressure typically at 100 psig (790 kPa). GC analyses were taken to verify feed composition. The feed was then pumped through the catalyst bed held at the reaction temperature of 350° C. to 460° C. at a WHSV of 2 and a pressure of 15-200 psig (204-1480 kPa). The liquid products exiting the reactor flowed through heated lines routed to two collection pots in series, the first pot being heated to 60° C. and the second pot cooled with chilled coolant to about 10° C. Material balances were taken at 12 to 24 hr intervals. Samples were taken and diluted with 50% ethanol for analysis. The non-condensable gas products were routed to an on line HP 5890™ GC.

The dehydrogenation product was analyzed on an Agilent 7890™ GC with 150 vial sample tray at the following conditions:

Inlet Temp: 220° C.;
Detector Temp: 240° C.;
Temp Program: Initial temp 120° C. hold for 15 min., ramp at 2° C./min to 180° C., hold 15 min; ramp at 3° C./min. to 220° C. and hold till end;
Column Flow: 2.25 ml/min. (27 cm/sec); Split mode, Split ratio 100:1;
Injector: Auto sampler (0.2 μl);
Column Parameters: Two columns joined to make 120 Meters (coupled with Agilent ultimate union, deactivated). Column #1 Front end: Supelco β-Dex 120; 60 m×0.25 mm×0.25 μm film joined to Column #2, back end: γ-Dex 325: 60 m×0.25 mm×0.25 μm film.

Figure 3:
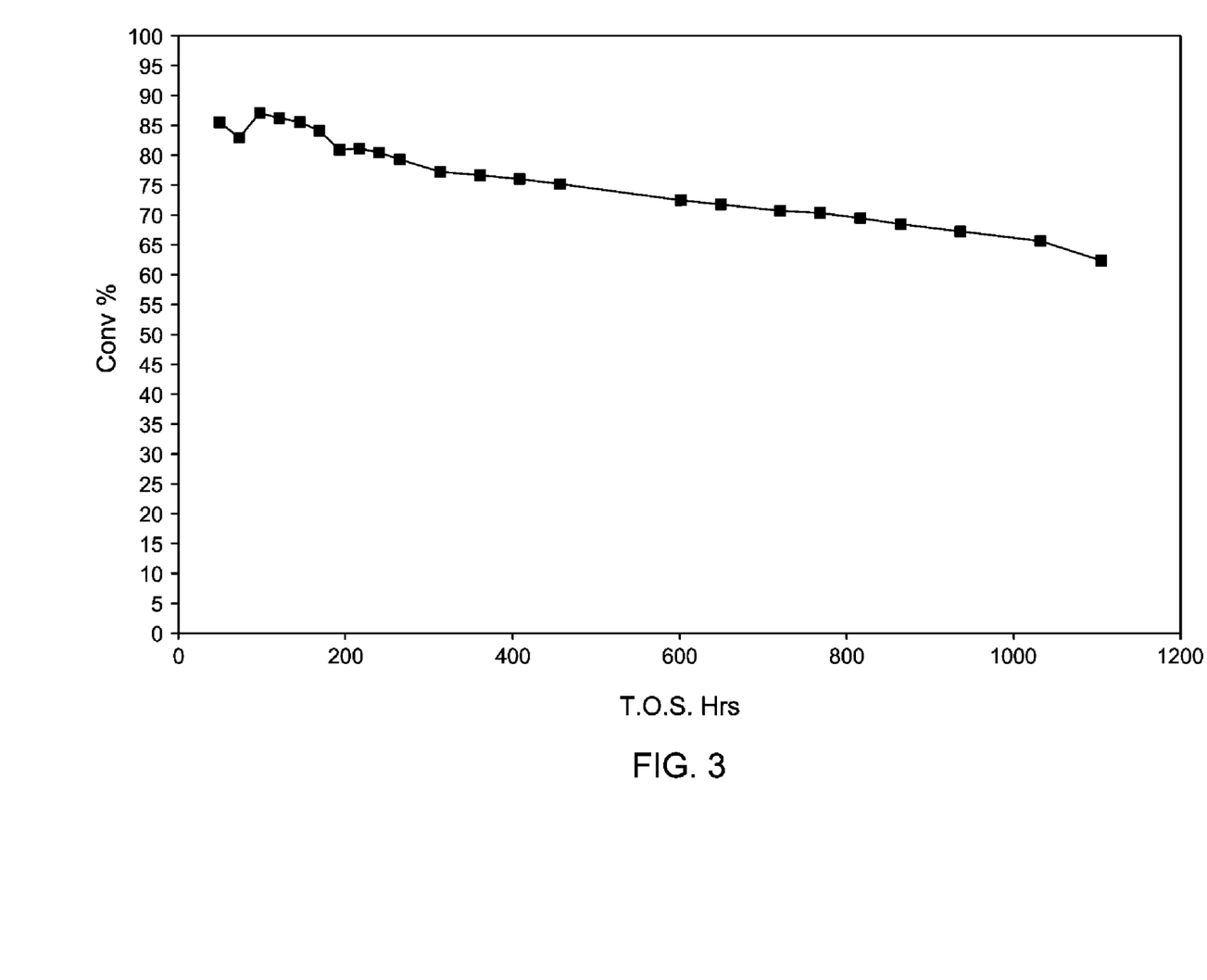
FIG. 3 is a graph of conversion of (methylcyclohexyl)toluene to dimethylbiphenyl against time on stream (T.O.S.) in the dehydrogenation of Example 4.
Figure 4:
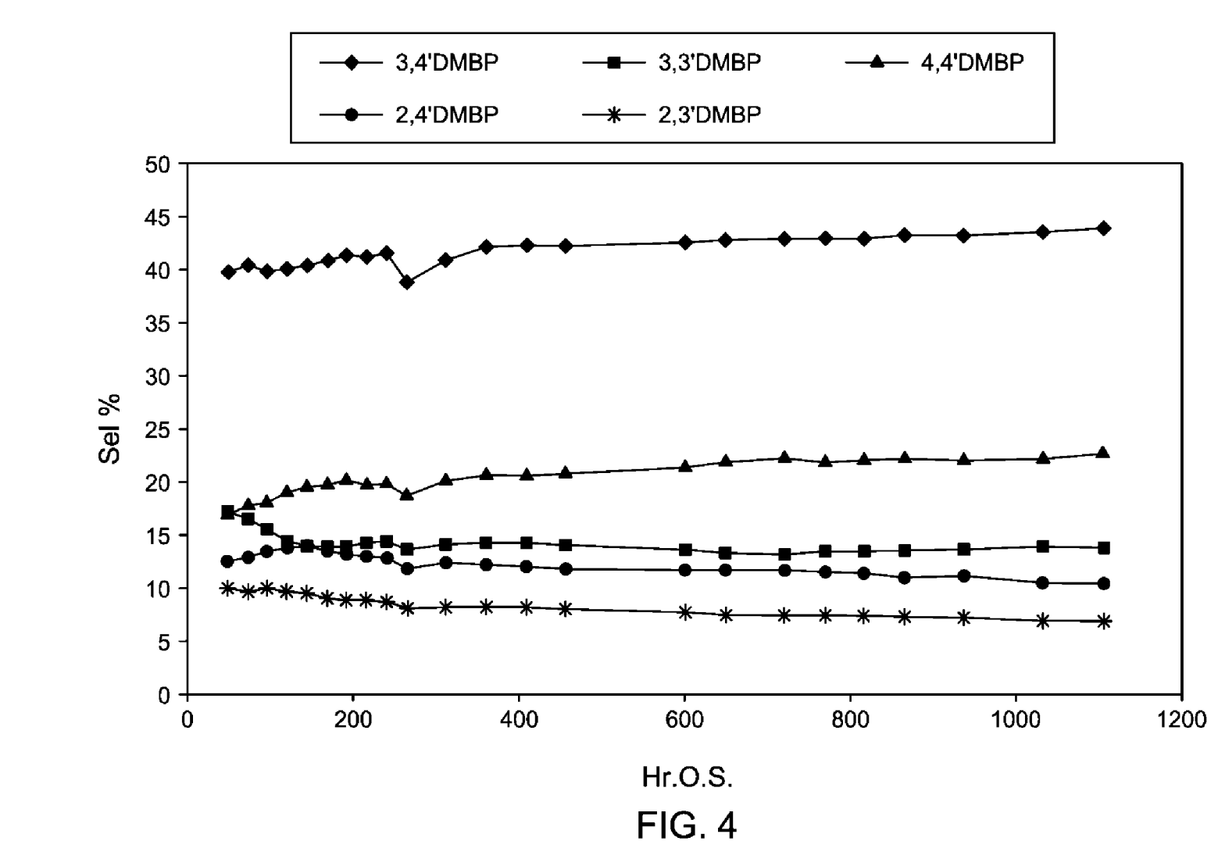
FIG. 4 is a graph of selectivity towards various dimethylbiphenyl isomers against T.O.S. in the dehydrogenation of Example 4.

The results of the dehydrogenation testing are summarized in FIGS. 3 and 4. The conversion of dimethylbicyclohexanes against time on stream (T.O.S.) is shown in FIG. 3, and the selectivity to various isomers against T.O.S. is shown in FIG. 4.

Example 5: Hydrogenation of Hydroalkylation Product (Inventive)

Toluene and methylcyclohexane were first removed from a 2 L sample of the hydroalkylation product of Example 4.

In a 300-mL Parr autoclave, 150.0 g of the residue and 2 g of a 0.3% Pt/0.9% Pd hydrogenation catalyst on Al support were pressurized with hydrogen at a gauge pressure of 1000 psig (6996 kPa) and heated to 200° C. while being stirred (1000 rpm). Samples were taken during the test run time, after which the autoclave was allowed to cool down to room temperature and the contents collected as the hydrogenation product. The concentrations of the hydrogenated product against T.O.S were measured, from which it was determined that 100% conversion of (methylcyclohexyl)toluene was obtained.

Example 6: Dehydrogenation of Hydrogenation Product (Inventive)

The hydrogenation product from Example 5 was mixed with toluene (90:10 toluene:hydrogenated product) and dehydrogenated in accordance with the conditions of Example 4. The conversion of dimethylbicyclohexane against T.O.S. is shown in FIG. 5, and the selectivity to various isomers against T.O.S. is shown in FIG. 6.

Figure 5:
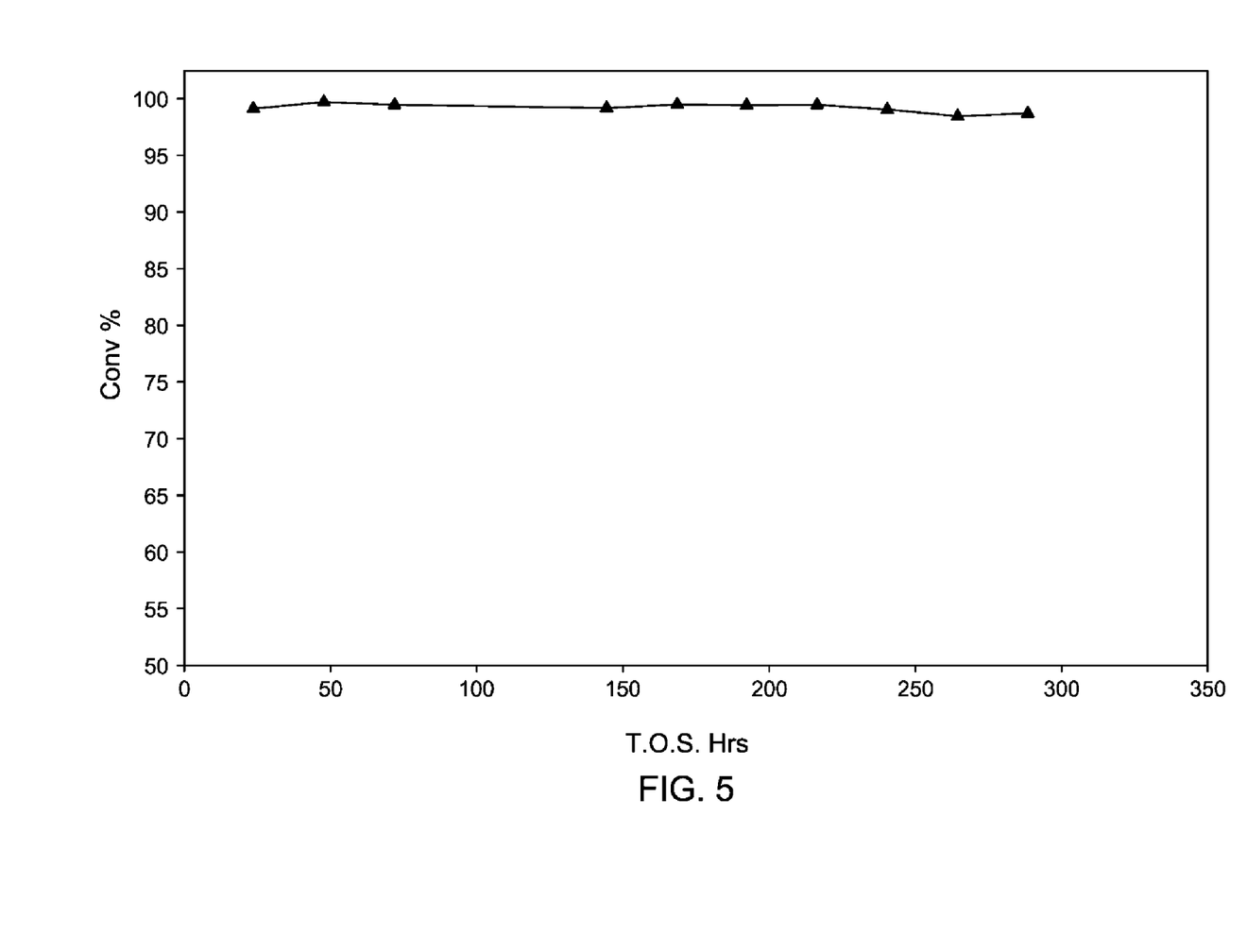
FIG. 5 is a graph of conversion of dimethylbicyclohexane to dimethylbiphenyl against T.O.S. in the dehydrogenation of Example 6.

It can be seen from FIGS. 3 and 5 that both the conversion of dimethylbicyclohexanes and the resistance of the catalyst to deactivation were enhanced by hydrogenating the hydroalkylation product prior to dehydrogenation. For example, in Example 6, where the hydroalkylation product was hydrogenated prior to dehydrogenation, more than 99% conversion was obtained and the catalyst remained stable over the measured timeframe of 300 hours with no indication of deactivation. In contrast, in Example 4, where dehydrogenation was conducted directly after hydroalkylation, about 85% or less conversion was obtained and the catalyst showed signs of deactivation within the first 300 hours. These results demonstrate that utilization of an intermediate hydrogenation step followed by dehydrogenation, compared to direct dehydrogenation of the hydroalkylation product, inhibited the deactivation of the dehydrogenation catalyst and improved the catalyst activity and stability.

Figure 6:
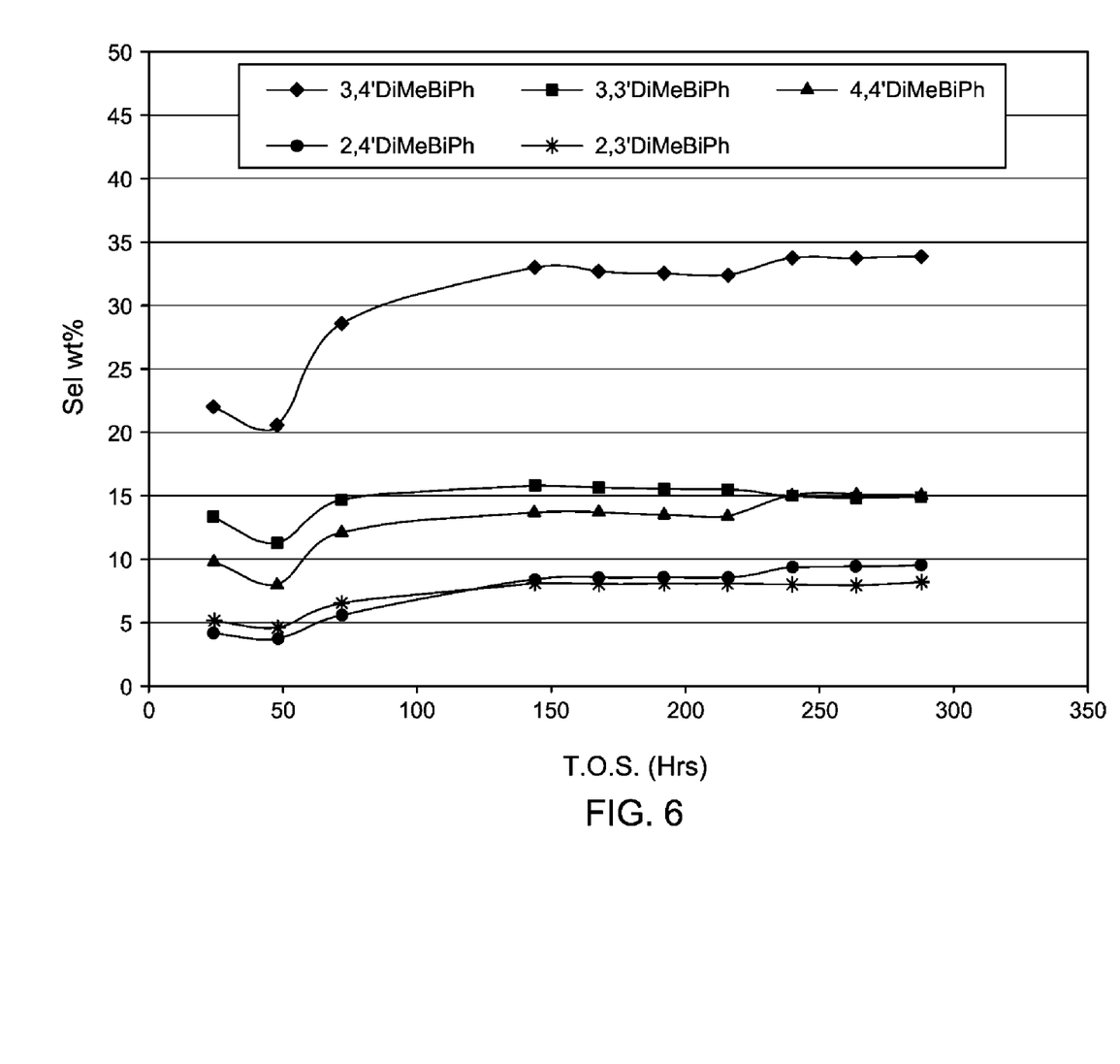
FIG. 6 is a graph of selectivity towards various dimethylbiphenyl isomers against T.O.S. in the dehydrogenation of Example 6.

It can also be seen from FIGS. 4 and 6 that the selectivity to the desired isomeric product mixture was enhanced by hydrogenating the hydroalkylation product prior to dehydrogenation. In particular the percentage of undesired 2.3'-dimethylbipheny ("2,3'-DiMeBiPh") and 2,4'-dimethylbiphenyl ("2,4'-DiMeBiPh") isomers in Example 6, where the hydroalkylation product was hydrogenated prior to dehydrogenation, was lower than that in Example 4, where dehydrogenation was performed directly after hydroalkylation. These results demonstrate that utilization of an intermediate hydrogenation step followed by dehydrogenation achieves enhanced selectivity to the desired 3.4'-, 3,3'-, and 4,4'-dimethylbiphenyls ("3,4'-DiMeBiPh", "3,3'-DiMeBiPh", and "4,4'-DiMeBiPh"), which are favorable in the subsequent production of esters.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:
1. A process for producing a methyl-substituted biphenyl compound, the process comprising:
   (a) providing a mixture comprising at least one methyl-substituted cyclohexylbenzene compound of the formula (I) below:

wherein step (a) further includes,
      (a-1) contacting a feed comprising at least one aromatic hydrocarbon selected from the group consisting of toluene, xylene and mixtures thereof with hydrogen in the presence of a hydroalkylation catalyst under conditions effective to produce a hydroalkylation reaction product comprising methyl-substituted cyclohexylbenzene compounds,
      (a-2) dehydrogenating at least part of the methyl-substituted cyclohexylbenzene compounds in the hydroalkylation reaction product in the presence of the dehydrogenation catalyst under conditions effective to produce a dehydrogenation reaction product comprising methyl-substituted biphenyl compounds and unreacted methyl-substituted cyclohexylbenzene compounds, and
      (a-3) separating at least part of the unreacted methyl-substituted cyclohexylbenzene compounds from the dehydrogenation reaction product to form the mixture;
   (b) contacting at least part of the mixture with hydrogen in the presence of a hydrogenation catalyst under conditions effective to produce a hydrogenation reaction product comprising at least one methyl-substituted bicyclohexane compound of the formula (II) below;

wherein each of m and n in formulas (I) and (II) is independently 1, 2, or 3, wherein the hydrogenation reaction product from step (b) comprises less than about 30 wt % of 1, X'- and/or 2-X'-isomers of methyl-substituted bicyclohexane based on the total weight of the isomers of methyl-substituted bicyclohexane, wherein X' is 2', 3', or 4'; and
   (c) contacting at least part of the hydrogenation reaction product with a dehydrogenation catalyst under conditions effective to produce a dehydrogenation reaction product comprising at least one methyl-substituted biphenyl compound.
2. The process of claim 1, wherein each of m and n is, independently, 1 or 2.
3. The process of claim 1, wherein step (a-2) is carried out in a reaction vessel, and wherein the hydrogenation product of step (b) is recycled to the reaction vessel so that step (c) is carried out in the reaction vessel.

4. The process of claim 1, wherein the mixture further comprises 2, X'-isomers of methyl-substituted biphenyl compounds, wherein X' is 2', 3', or 4'.

5. The process of claim 1, wherein the hydrogenation reaction product from step (b) comprises less than about 20 wt % of 2, X' isomers of methyl-substituted bicyclohexane based on the total weight of the isomers of methyl-substituted bicyclohexane.

6. The process of claim 1, wherein the dehydrogenation reaction product from step (c) comprises less than about 20 wt % of 2, X' isomers based on the total weight of the isomers of the methyl-substituted biphenyl compounds, wherein X' is 2', 3', or 4'.

7. The process of claim 1, wherein the hydrogenation catalyst comprises at least one member selected from the group consisting of Pd, Pt, Rh, Ru, Os, Ir, Ni, Zn, Sn, Co, combinations thereof, compounds thereof, and mixtures of compounds thereof.

8. The process of claim 7, wherein the hydrogenation catalyst comprises Pd and/or Pt.

9. The process of claim 1, wherein the hydrogenation catalyst further comprises a molecular sieve selected from the group consisting of BEA, FAU, MTW, and MWW structure type molecular sieves.

10. The process of claim 9, wherein the hydrogenation catalyst comprises a molecular sieve of the MCM-22 family.

11. The process of claim 1, wherein the hydrogenation conditions comprise a temperature of from about 50° C. to about 400° C. and a pressure of from about 100 kPa to about 10,000 kPa.

12. The process of claim 1, wherein the hydroalkylation catalyst comprises an acidic component and a hydrogenation component.

13. The process of claim 12, wherein the acidic component is selected from the group consisting of BEA, FAU, MTW, and MWW structure type molecular sieves, and the hydrogenation component is selected from the group consisting of Pd, Ru, Ni, Zn, Sn, Co, combinations thereof, compounds thereof, and mixtures of compounds thereof.

14. The process of claim 13, wherein the molecular sieve is a molecular sieve of the MCM-22 family.

15. The process of claim 1, wherein the conditions in step (a-1) comprise a temperature of from about 100° C. to about 400° C. and a pressure of from about 100 kPa to about 7,000 kPa.

16. The process of claim 1, wherein the molar ratio of hydrogen to aromatic feed supplied to the contacting (a-1) is from about 0.15:1 to about 15:1.

17. The process of claim 1, wherein the dehydrogenation catalyst comprises an element or compound thereof selected from Group 10 of the Periodic Table of Elements.

18. The process of claim 17, wherein the dehydrogenation catalyst further comprises tin or a compound thereof.

19. The process of claim 1, wherein the dehydrogenation conditions in step (c) and/or step (a-2) comprise a temperature of from about 200° C. to about 600° C. and a pressure of from about 100 kPa to about 3550 kPa.

20. A process for producing a biphenyl ester, comprising:
producing at least one methyl-substituted biphenyl compound according to claim 1;
contacting the at least one methyl-substituted biphenyl compound with an oxygen source under conditions effective to produce a biphenyl carboxylic acid; and
reacting the biphenyl carboxylic acid with one or more $C_4$ to $C_{14}$ alcohols under conditions effective to produce the biphenyl ester.

* * * * *